(12) United States Patent
Souffrou

(10) Patent No.: US 11,315,680 B2
(45) Date of Patent: *Apr. 26, 2022

(54) SYSTEM AND METHOD FOR MANAGING MEDICAL DEVICE INVENTORY

(71) Applicant: SXANPRO, Grand Rapids, MI (US)

(72) Inventor: Ashlea Souffrou, Grand Rapids, MI (US)

(73) Assignee: SXANPRO, Grand Rapids, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/471,639

(22) Filed: Sep. 10, 2021

(65) Prior Publication Data

US 2021/0407662 A1 Dec. 30, 2021

Related U.S. Application Data

(63) Continuation-in-part of application No. 16/275,071, filed on Feb. 13, 2019, now Pat. No. 11,120,399.

(51) Int. Cl.
| | |
|---|---|
| *G16H 40/20* | (2018.01) |
| *A61B 90/96* | (2016.01) |
| *G16H 40/63* | (2018.01) |
| *G06Q 10/08* | (2012.01) |

(52) U.S. Cl.
CPC ............ *G16H 40/20* (2018.01); *A61B 90/96* (2016.02); *G06Q 10/087* (2013.01); *G16H 40/63* (2018.01)

(58) Field of Classification Search
CPC .. G06Q 10/087; G06Q 10/0875; G16H 40/20; G16H 40/63; A61B 90/96

USPC ............................................................ 705/29
See application file for complete search history.

(56) References Cited

U.S. PATENT DOCUMENTS

| | | | |
|---|---|---|---|
| 8,645,156 B2 | 2/2014 | Ravazzolo | |
| 9,250,712 B1 | 2/2016 | Todeschini | |
| 9,990,603 B2 | 6/2018 | Kerrick | |
| 10,013,669 B2 | 7/2018 | McCullough et al. | |
| 10,152,688 B2 | 12/2018 | DeBusk et al. | |
| 2003/0055753 A1 | 3/2003 | Dellar et al. | |
| 2008/0086387 A1* | 4/2008 | O'Rourke | G06Q 30/0601 705/26.1 |
| 2013/0087609 A1* | 4/2013 | Nichol | G06F 16/23 235/375 |
| 2014/0288952 A1 | 9/2014 | Smith et al. | |
| 2016/0371639 A1* | 12/2016 | Smith | G16H 40/20 |

* cited by examiner

*Primary Examiner* — Allen C Chein
*Assistant Examiner* — Denisse Y Ortiz Roman
(74) *Attorney, Agent, or Firm* — Polsinelli PC

(57) ABSTRACT

A system for medical device inventory management is disclosed. The system is comprised of at least one scanner to scan medical device information associated with a medical device. The at least one scanner is in operable communication with at least one computing device configured to receive the medical device information from the scanner. A processor is in operable communication with the computing device and an interpreter adapted to transpose the medical device information to a graphical user interface. An inventory module is in operable communication with the processor to inventory the medical device information, including preparing a list of a plurality of medical devices. A document generator is in operable communication with the computing device to generate a document in a shareable format.

22 Claims, 6 Drawing Sheets

SYSTEM AND METHOD FOR MANAGING MEDICAL DEVICE INVENTORY

CROSS-REFERENCE TO RELATED APPLICATIONS

This application is a continuation-in-part of U.S. application Ser. No. 16/275,071, now U.S. Pat. No. 11,120,399, filed Feb. 13, 2019, the contents of which are entirely incorporated by reference herein.

TECHNICAL FIELD

The embodiments generally relate to an inventory management and control system and, more specifically, to an inventory management and control system for the medical device industry.

BACKGROUND

Manufacturers, suppliers, and retailers alike each undergo the difficulty of managing inventory of their products. In the past, inventory was recorded manually leading to a significant loss of resources and a high propensity for errors. In recent years optical scanners have been used to identify product information and transmit the information to a readable medium.

While a variety of industries utilize various forms of electronic inventory management, the medical device industry has a low tolerance for errors throughout the inventory process due to the potential liability of harming a client due to inaccurate records.

Medical device inventory systems currently available are unable to scan and record the expiration date and lot number of a particular device in a standalone software package. This inability inconveniences various parties within the medical device industry including nurses, physicians, and medical device sales representatives and suppliers as users are required to utilize multiple software platforms to perform inventory tasks.

SUMMARY OF THE INVENTION

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

The embodiments described herein provide a system for medical device inventory management. The system is comprised of at least one scanner to scan medical device information associated with a medical device. The at least one scanner is in operable communication with at least one computing device configured to receive the medical device information from the scanner. A processor is in operable communication with the computing device, and an interpreter adapted to interpret the medical device information and transpose the medical device information to a graphical user interface. An inventory module is in operable communication with the processor to inventory the medical device information including preparing a list of a plurality of medical devices. A document generator is in operable communication with the computing device to generate a document in a shareable format.

In one aspect, the medical device information is comprised of a unique device identifier, a lot number, an expiration date, a model number, a serial number, date of manufacture, package type, package quantity, and recall information, and/or a manufacturer description.

In one aspect, the medical device information is comprised of a static part and a dynamic part. The static part is pulled from an external database and may be stored on a local database. The external database may, in some aspects, be a Food and Drug Administration database.

In one aspect, the graphical user interface is comprised of a device details interface wherein medical device information is manually input.

Some embodiments provide for a method for facilitating the management of medical device inventory. The method comprises the steps of scanning, via a scanner in communication with a computing device, a first plurality of medical device information associated with a medical device. The first plurality of medical device information may include but is not limited to a unique device identifier (UDI), a lot number, an expiration date, a serial number, and a manufacture date. A processor may then interpret the medical device information using an interpreter. A second plurality of medical device information is pulled from an external database stored locally. The second plurality of medical device information may include, but is not limited to, a model number, a manufacturer, a manufacturer description, package type, package quantity, and/or FDA recall information. The first and second pluralities of medical device information are then logged into a database and displayed on the computing device.

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

Figure 1:
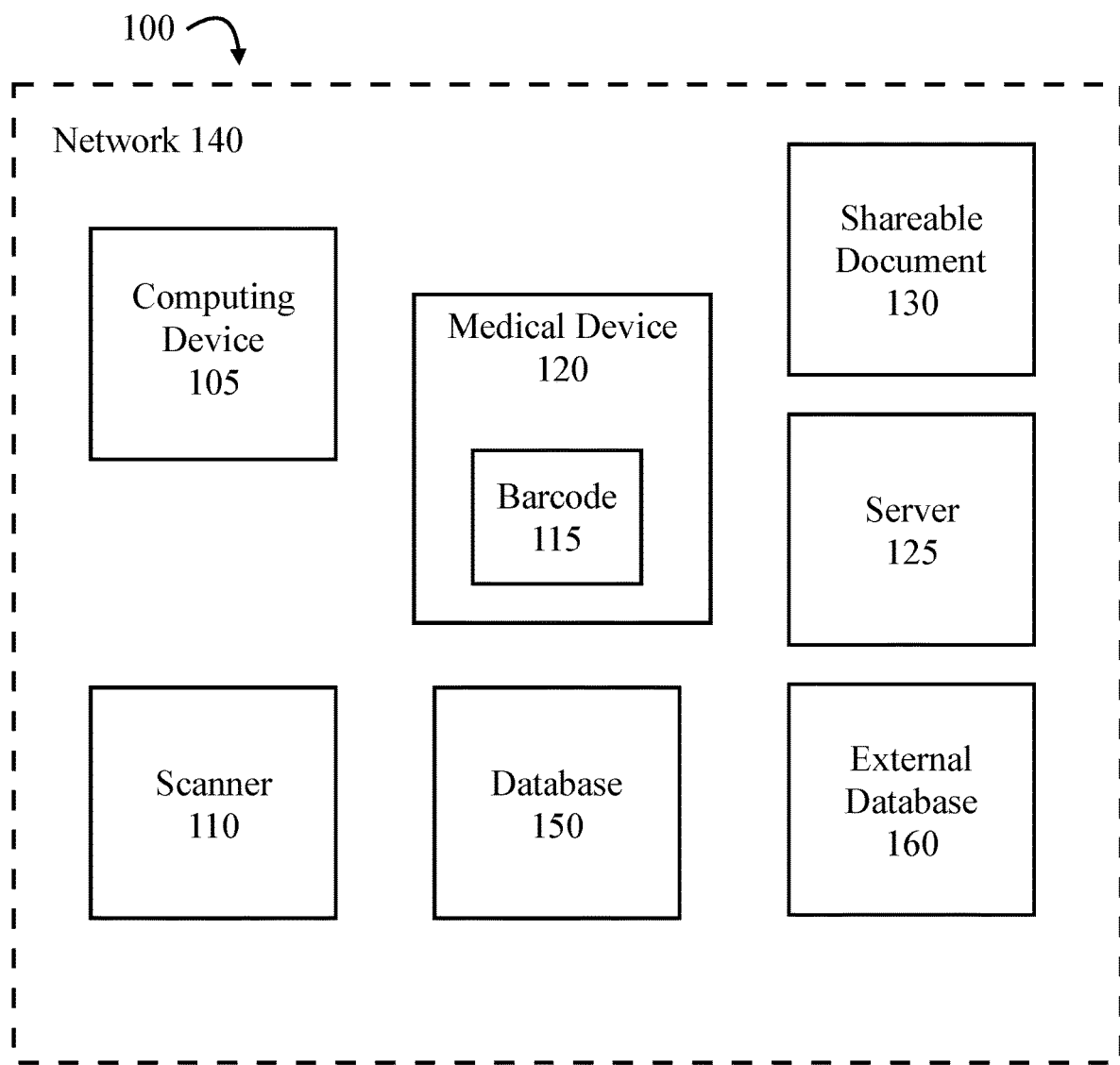
FIG. 1 illustrates a block diagram of the network infrastructure, according to some embodiments.

The specific details of the single embodiment or variety of embodiments described herein are to the described system and methods of use. Any specific details of the embodiments are used for demonstration purposes only, and no unnecessary limitations or inferences are to be understood therefrom.

Before describing in detail exemplary embodiments, it is noted that the embodiments reside primarily in combinations of components and procedures related to the system and method. Accordingly, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Some embodiments disclosed herein significantly improve the ability of medical device manufacturers, care providers, healthcare professionals, medical device suppliers, and medical device sales representatives to manage inventory. Aspects of the embodiments provide an improved service offering by providing functionalities either not present or in a more simplified form than is disclosed in the current arts of the medical device industry and similar product-based industries alike.

Some embodiments may provide an inventory management system configured to be applied to the medical device industry, a user interface for engaging with inventory data and data present in one or more external and/or local databases, such as the Food and Drug Administration (FDA) databases, and electronic data capture hardware and software systems.

As used herein, the term "medical device information" is used to describe any information provided on a medical device including, but not limited to, a unique device identifier (UDI), lot number, expiration date, serial number, date of manufacture, model number, catalog number, a manufacturer name, manufacturer description, package type, package quantity, and recall information. In some examples, the medical device information may be divided into a first plurality of medical device information (a dynamic part) and a second plurality of medical device information (a static part). The first plurality of medical device information may be dynamic because it may change between individual devices of the same model. For example, the first plurality of information may include, but is not limited to a UDI, a lot number, an expiration date, a serial number, and a manufacture date. The UDI includes a unique numeric or alphanumeric code and/or a machine-readable form that uses automatic identification and data capture (AIDC) technology that identifies the labeler and the specific version or model of a device. The UDI may further include the lot or batch number, serial number, expiration date, and date of manufacture. In some examples, the first plurality of medical device information may be the UDI. The second plurality of data may be obtained from an external or local database storing information from the FDA UDI database using the UDI code that was interpreted from the first plurality of medical device information. The second plurality of medical device information may include, but is not limited to, a model number, a manufacturer, a manufacturer description, package type, package quantity, and/or FDA recall information.

As used herein, the term "medical device" is used to describe any device, apparatus, material, or system used in the medical field, such as in a hospital, clinic, or physician's office. The medical device may be disposable with an expiration date or may be reusable without a standard expiration date. In some examples, the medical device may be capital equipment used over multiple years with multiple patients.

As used herein, "expiration date" is used to refer to the date of expiration as provided by the manufacturer. In some embodiments, when the medical device is capital equipment, the expiration date may be a recommended replacement date.

FIG. 1 illustrates an exemplary architecture of the inventory management system 100 implemented in the various embodiments disclosed herein. The system 100 is comprised of at least one computing device 105 in communication with a scanner 110. The scanner 110 may be integrated within the computing device 105 or provided as a separate hardware component as known in the arts. The scanner 110 reads a barcode 115 provided on the medical device 120. In some aspects, the barcode is the machine-readable form of the UDI. The computing device 105, via the scanner 110 and interpreter, determines a first plurality of medical device information, such as a UDI, a lot number, an expiration date, a serial number, and/or date of manufacture. The first plurality of information may be used to determine a second plurality of medical device information stored in one or more local databases. The second plurality of medical device information may include, but is not limited to, a model number, a manufacturer, a manufacturer description, package type, package quantity, and/or FDA recall information. A server 125 is operable to transmit, via network 140, the medical device information to the computing device 105, or to an external computing system to interpret the medical device information and transpose the medical device information into a shareable document 130 viewable on a printed medium, or on the graphical user interface of the computing device 105. Database 150 is configured to store medical device information and data associated with the system 100. In some embodiments, one or more external databases 160 may be utilized to aggregate and pull data. The external database 160 may be comprised of the Food and Drug Administration (FDA) database, in addition to various additional external databases. In an embodiment, the FDA database is the FDA UDI database. In some embodiments, the external database, such as the FDA UDI database or a recall database, is downloaded and stored in one or more local databases.

The computing device 105 may include conventional components such as one or more memory components and one or more processors. Examples of computing devices include such known mobile devices as smartphones, tablets. etc., but it should be understood that the computing device need not be a mobile device and the inventive concepts apply to other computing devices such as a desktop computer or stand-alone scanning/computing device.

In some embodiments, the scanner 110 is any electronic data capture system with image scanning and/or barcode scanning capabilities as known in the arts. The scanner 110 may be specially adapted to scan and read barcodes provided on a medical device. In other embodiments, the scanner 110 may be part of the computing device 105. For example, the scanner 110 may be the camera integrated in a mobile device. In additional embodiments, the scanner 110 scans a barcode, QR code, UDI, and/or RFID tag to determine the information of the medical device. Once the medical device information has been determined, the system renders a visual of the medical device information on the graphical user interface (GUI) of the computing device 105.

The system 100 can include or be associated with a plurality of databases that include information for the system 100, inventory lists, and medical device information lists, generated by the system, which can be local, stored somewhere else and accessible using the network 140, generated as needed from various data sources, or some combination of these. For example, the system 100 may include a local database for storing the FDA UDI database. The system 100 may pull the FDA UDI database from the FDA at regular intervals to update the local database. In some embodiments, the local database storing the information from the FDA UDI database may be updated yearly, quarterly, monthly, semi-monthly, weekly, or daily. Having the external database stored locally allows for the system 100 to access the information in the database without requiring access to the internet. This may be useful when the system is being used in basements or other areas of a hospital without reliable access to the internet.

Figure 2:
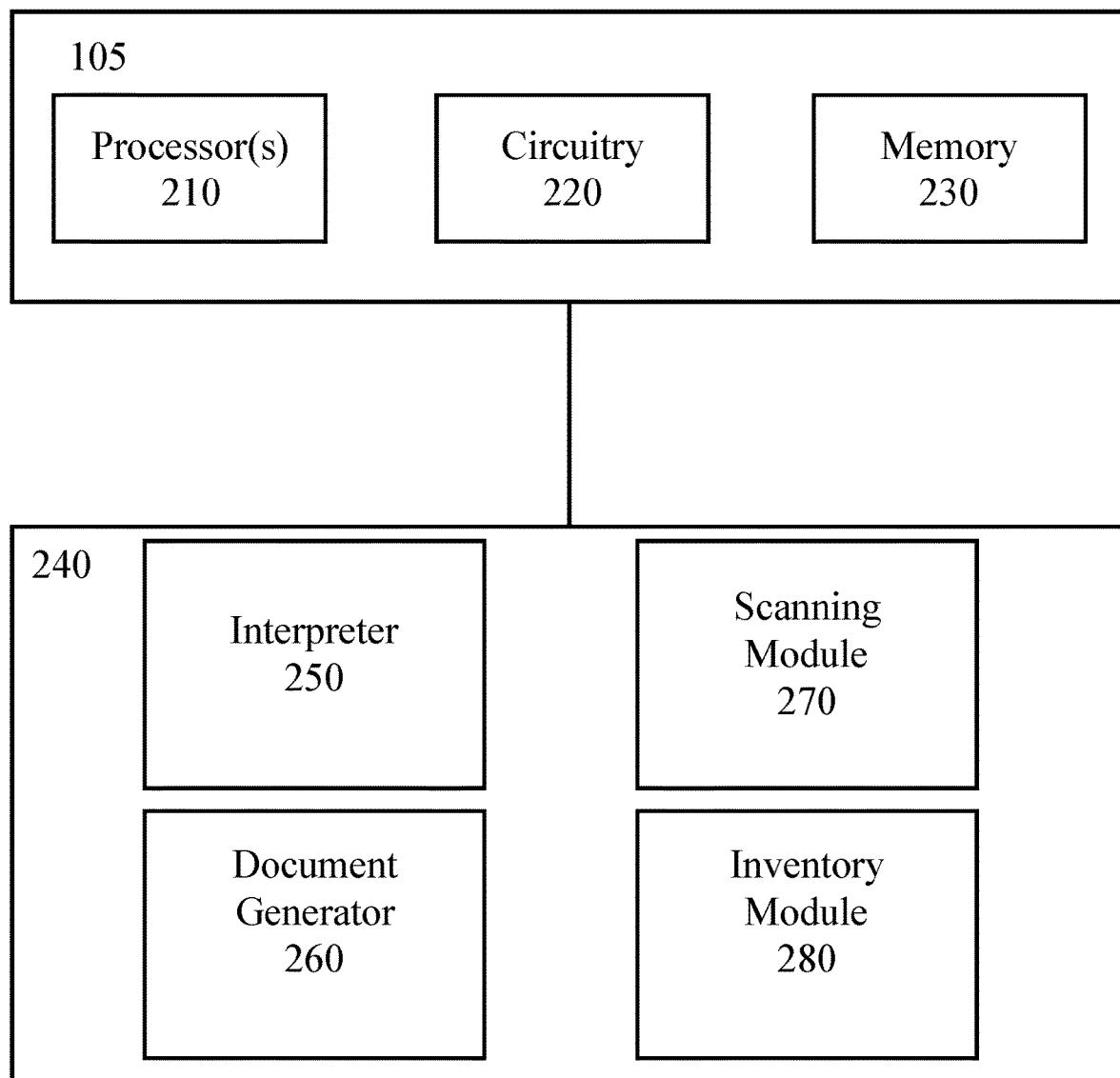
FIG. 2 illustrates a block diagram of the program logic and associated modules, according to some embodiments.

FIG. 2 illustrates a component level diagram of the computing device 105 utilized to perform the various embodiments disclosed herein. The computing device is comprised of at least one processor 210 connected via circuitry 220 to a memory 230 operable to perform program logic 240. The program logic 240 includes a plurality of code to perform various functions of the embodiments including an interpreter 250, a document generator 260, a scanning module 270, and an inventory module 280. In some aspects of the embodiments, the interpreter 250 receives medical device information from the scanning module 270 and interprets the information to create a list of medical devices using an inventory module 280. In an embodiment, the interpreter 250 receives the first plurality of medical device information and interprets the information such that one or more parts of the first plurality of medical device information may be used to pull the second plurality of medical device information. For example, the interpreter may receive the expiration date, serial number, lot number, date of manufacture, and/or the UDI number from the scanner. The first plurality of medical device information may then be logged in a system database and be used to create a list using the inventory module. In addition, the unique numeric or alphanumeric code of the UDI may be logged in the system database. The UDI may then be used to automatically look up the model number, manufacturer description, package type, package quantity, and/or FDA recall information from the local database storing information from the FDA UDI database. The second plurality of medical device information is logged in the system database with the first plurality of medical device information for that device. The first plurality of medical device information is aggregated with the second plurality of medical device information to create a combined entry for each medical device. The scanning and aggregation of medical device information may be done for a plurality of medical devices. The inventory module is in operable communication with the processor and is further operable to prepare a list of a plurality of medical devices, inventory the aggregated first and second pluralities of medical device information from the plurality of medical devices, and log the list of the plurality of medical devices and the inventory in the system database.

The processor may further be operable to generate alerts based off the medical device information. In an embodiment, the processor may generate an alert to the user if a medical device in the system database is approaching, at, or past its expiration date. For example, an alert may be generated if a medical device in the system database is within 90 days, 60 days, 30 days, 1 week, 6 days, 5 days, 4 days, 3 days, 2 days, or 1 day of expiring, or if it is currently expired. In some embodiments, the method may include generating an alert if the medical device currently being scanned is already expired or it is within 90 days, 60 days, 30 days, 1 week, 6 days, 5 days, 4 days, 3 days, 2 days, or 1 day of expiring. If the device is within 90 days, 60 days, 30 days, 1 week, 6 days, 5 days, 4 days, 3 days, 2 days, or 1 day of expiring, or expired, the processor generates a notice asking the user if the device should continue to be scanned. The alert may be a visual indicator displayed on the interface and/or may be an audible indicator.

In another embodiment, the processor may further be operable to generate an alert to the user that a medical device in the system database has an FDA recall. In another embodiment, the processor may further be operable to generate an alert to the user that a medical device currently being scanned has an FDA recall. The alert may include recall information from a local database, such as an FDA database stored locally. The alert may be a visual indicator displayed on the interface and/or may be an audible indicator.

A document generator 260 operates to transpose the medical device information listed in the inventory module 280 to a shareable document format. For example, a document generator 260 is in operable communication with the computing device 105 to transpose the inventoried aggregated first and second pluralities of medical device information from the system database to generate a document in a shareable format. The document may be viewable on the graphical user interface and/or exported to an external user.

Figure 3:
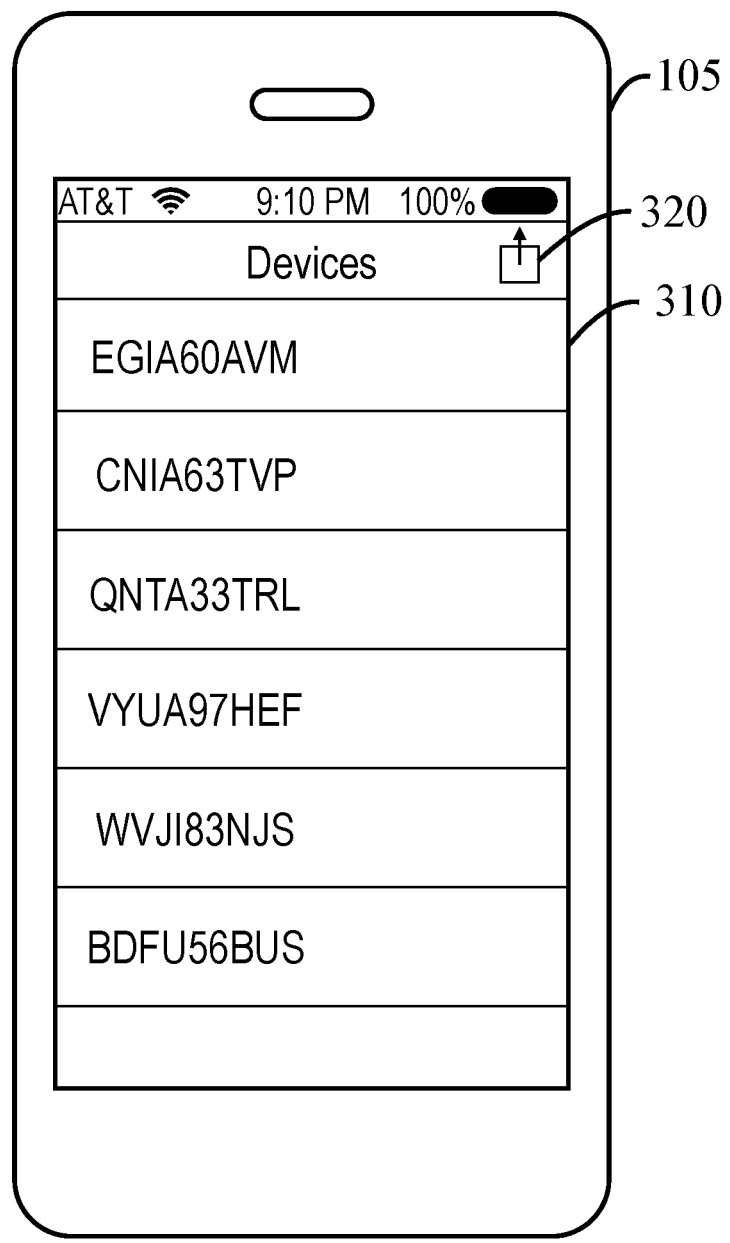
FIG. 3 illustrates a screenshot of the medical device inventory interface, according to some embodiments.

FIG. 3 illustrates a medical device inventory interface 310 displayed on the computing device 105. An export button 320 permits the medical device information displayed on the interface 310 to be transposed into a shareable document format, or exported to an external user via email or similar communications interface known in the arts. In some embodiments, all or part of the system database may be displayed on the interface 310. The interface 310 may be interactive such that a user may select a medical device listed in the system database to view more details about the particular medical device, such as the aggregated first and second pluralities of medical device information for the particular medical device.

Figure 4:
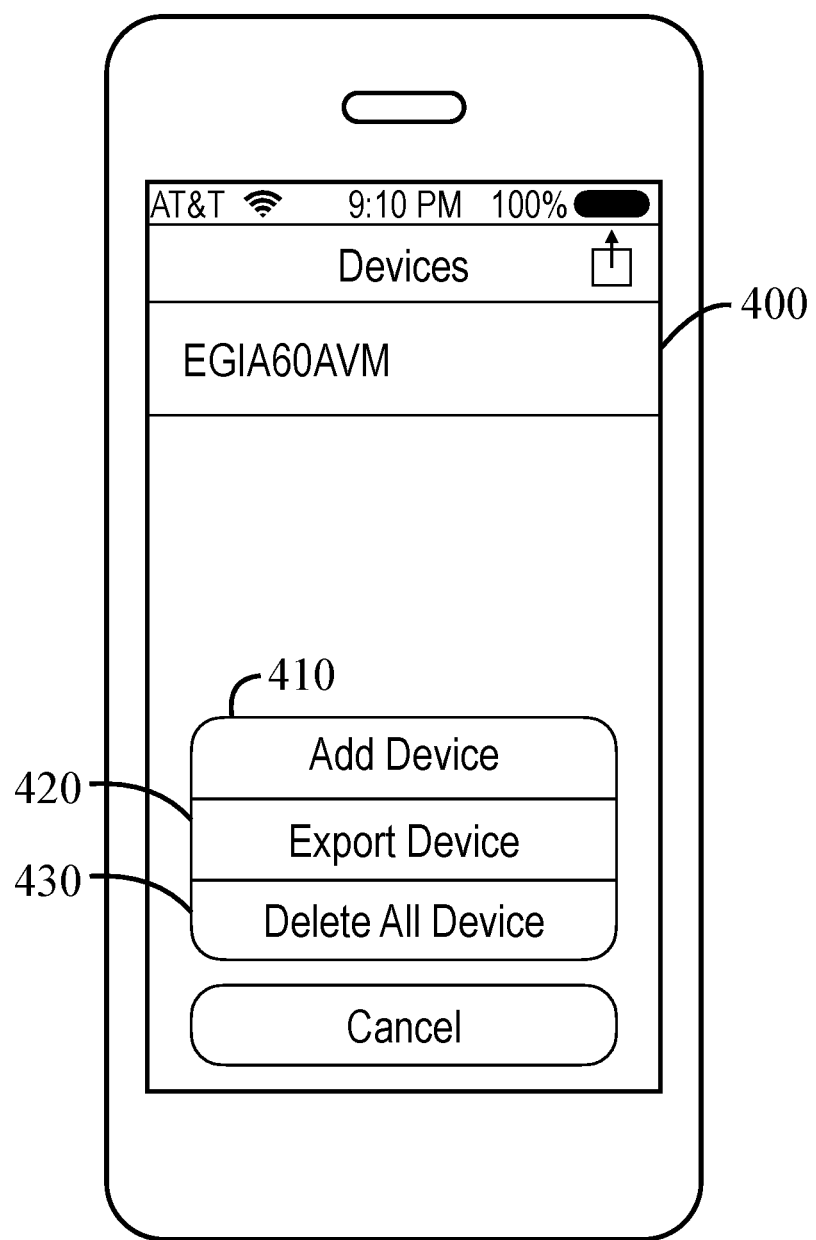
FIG. 4 illustrates a screenshot of the medical device input and export interface, according to some embodiments.
Figure 5:
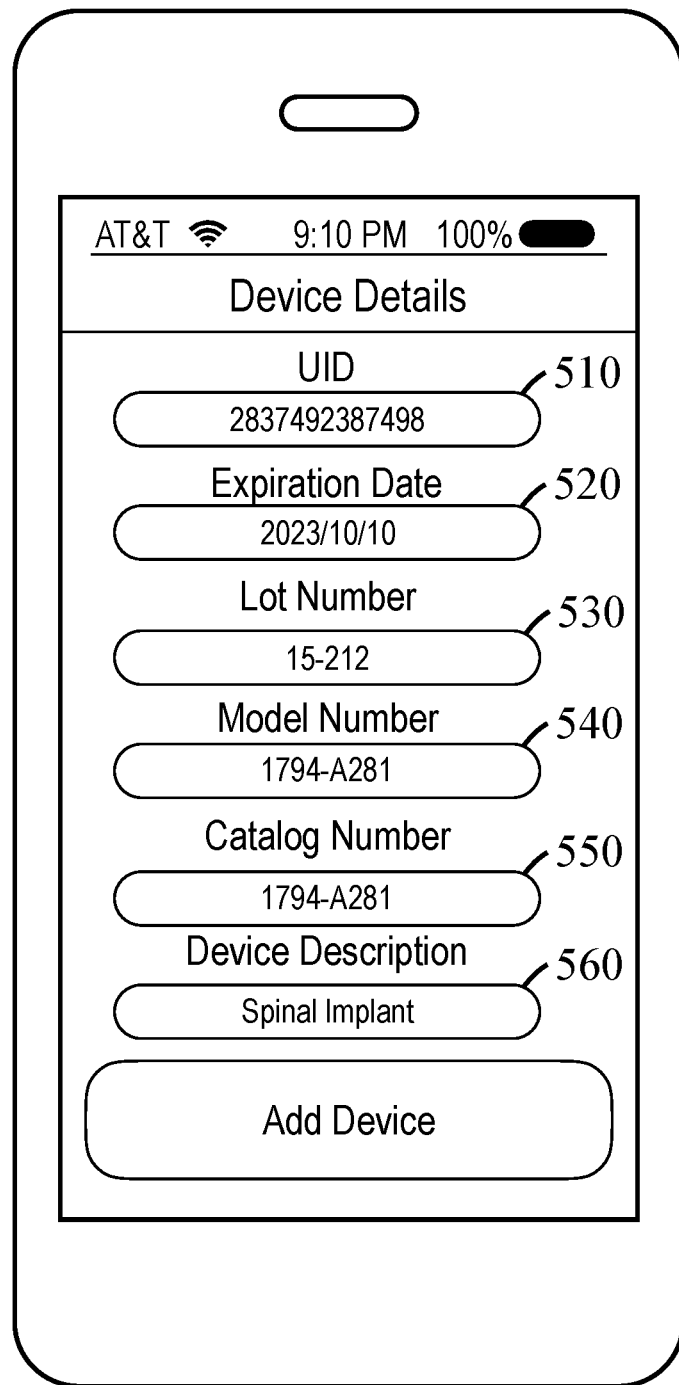
FIG. 5 illustrates a screenshot of the device details input interface, according to some embodiments.

FIG. 4 illustrates a medical device information export interface 400 which provides input buttons including an Add Device" input 410, "Export Device" input 420, and a "Delete All Devices" input 430. Selecting the "Add Device" input 410 transmits the user to the device input interface illustrated in FIG. 5 wherein the user is provided with a plurality of input fields. The plurality of input fields may be automatically populated with the first and/or second plurality of medical device information. The user may edit a field that was automatically populated or may fill in a blank field. For example, the user inputs medical device information including, but not limited to, a UDI input 510, an expiration date input 520, a lot number input 530, a model number input 540, a catalog number input 550, a device description input 560, serial number input, manufacture date input, UDI input, and quantity input. Each input, such as those provided in FIG. 5, may be automatically entered using the scanner in communication with the interpreter as described hereinabove.

In some embodiments the medical device information export interface 400 may include input buttons such as, but not limited to, the manufacturer name, packaging type, quantity, price, and the ability for the input of a comment or other form of information or description of the medical device.

Figure 6:
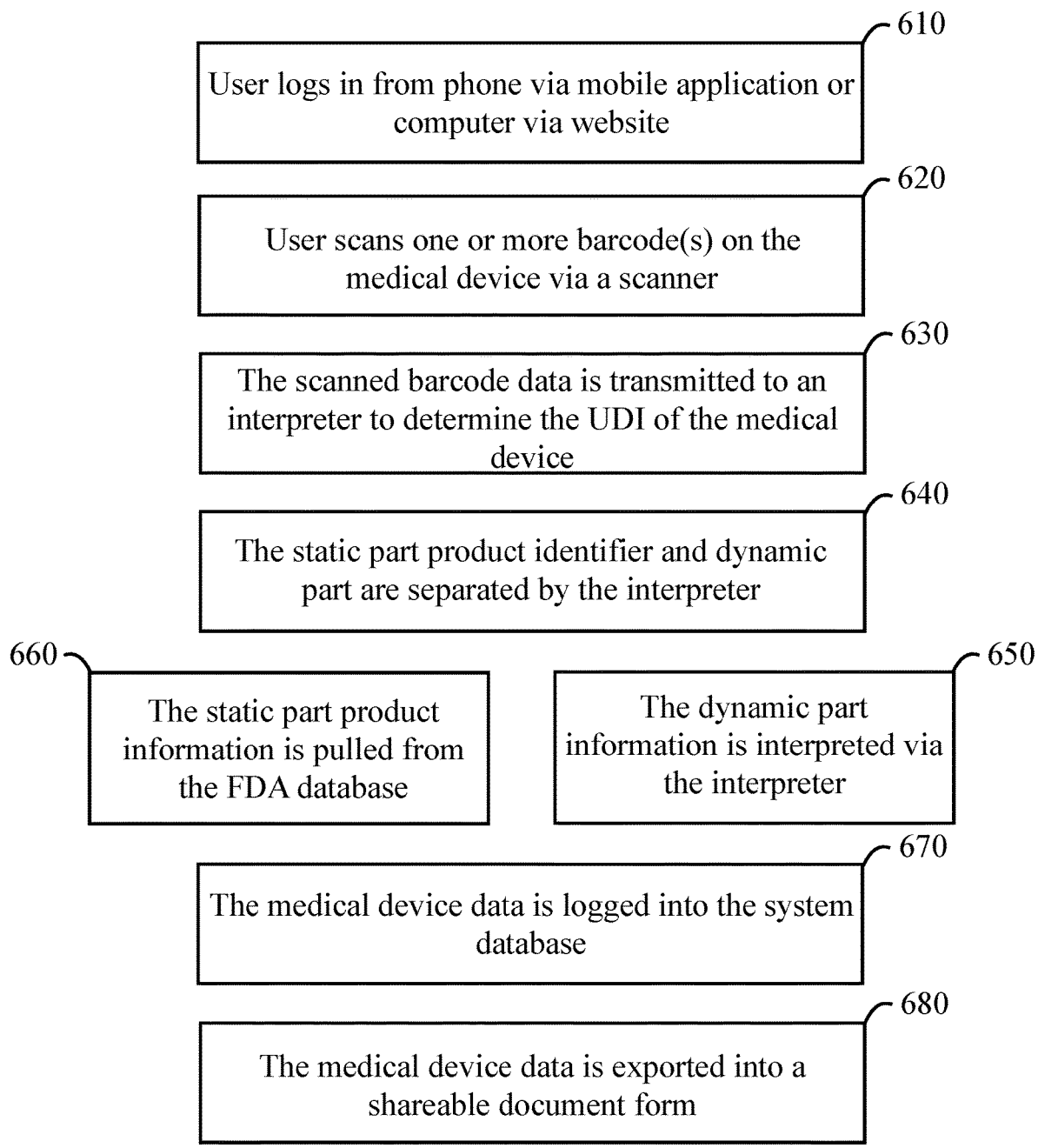
FIG. 6 illustrates a flowchart of a method of utilizing the medical device inventory management system, according to some embodiments.

FIG. 6 illustrates a flowchart of a method of using the system to manage medical device inventory. In step 610 the user accesses the system via the computing device and in step 620, scans the barcode on the medical device using the scanner. In step 630, the interpreter interprets the scanned barcode to identify the second plurality of medical device information (static part) and the first plurality of medical device information (dynamic part) of the barcode as shown in step 640. In step 650, the first plurality of medical device information (dynamic part) is interpreted via the interpreter, and in step 660, the second plurality of medical device information (static part) is pulled from an external database (such as the FDA database) or a local database containing data from the external database. In step 670, the first and second pluralities of medical device information are logged into the system database using the inventory module. Optionally, in step 680, the user may export the medical device information into a shareable document format. A plurality of medical devices may be scanned, such that the system database includes an inventory of the medical device information for the plurality of medical devices. All or part of the system database may be displayed on the interface.

In an embodiment, the method may further include generating an alert to the user if a medical device in the system database is approaching, at, or past its expiration date. For example, the method may include generating an alert if the medical device in the system database is within 90 days, 60 days, 30 days, 1 week, 6 days, 5 days, 4 days, 3 days, 2 days, or 1 day of expiring, or if it is currently expired. In some embodiments, the method may include generating an alert if the medical device being scanned is already expired or it is within 90 days, 60 days, 30 days, 1 week, 6 days, 5 days, 4 days, 3 days, 2 days, or 1 day of expiring. If the device is within 90 days, 60 days, 30 days, 1 week, 6 days, 5 days, 4 days, 3 days, 2 days, or 1 day of expiring, or expired, the method may further include generating a notice asking the user if the device should continue to be scanned. The alert may be a visual indicator displayed on the interface and/or may be an audible indicator.

In another embodiment, the method may further include generating an alert to the user that a medical device in the system database has an FDA recall. In another embodiment, the method may include generating an alert to the user that a medical device currently being scanned has an FDA recall. The alert may include recall information from a local database, such as an FDA database stored locally. The alert may be a visual indicator displayed on the interface and/or may be an audible indicator.

The steps and/or actions of a system described in connection with the embodiments disclosed herein may be embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor such that the processor can read information from, and write information to, the storage medium. In the alternative, the storage medium may be integrated into the processor. Further, in some embodiments, the processor and the storage medium may reside in an Application Specific Integrated Circuit (ASIC). In the alternative, the processor and the storage medium may reside as discrete components in a computing device. Additionally, in some embodiments, the events and/or actions of a method or algorithm may reside as one or any combination or set of codes and/or instructions on a machine-readable medium and/or computer-readable medium, which may be incorporated into a computer program product.

Also, any connection may be associated with a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc," as used herein, include compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

Processors suitable for the execution of a computer program include both general and special purpose microprocessors and any one or more processors of any digital computing device. The processor will receive instructions and data from a read-only memory or a random-access memory or both. The essential elements of a computing device are a processor for performing actions in accordance with instructions and one or more memory devices for storing instructions and data. Generally, a computing device will also include, or be operatively coupled to receive data from or transfer data to, or both, one or more mass storage devices for storing data, e.g., magnetic, magneto-optical disks, or optical disks; however, a computing device need not have such devices. Moreover, a computing device can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A computer-implemented system for medical device inventory management, the system comprising:
   at least one scanner configured to scan a barcode provided on a medical device for a first plurality of medical device information associated with the medical device, the at least one scanner integrated within a computing device configured to receive the first plurality of medical device information from the scanner, wherein the first plurality of medical device information comprises at least an expiration date, lot number, and a unique device identifier (UDI) for the medical device;

a processor in operable communication with the computing device, the processor adapted to: interpret the first plurality of medical device information, via an interpreter; automatically pull from a local database a second plurality of medical device information associated with the medical device based on the interpreted first plurality of medical device information, wherein the second plurality of medical device information is stored on the local database comprising information from a Food and Drug Administration UDI database, the second plurality of medical device information comprising a model number and a device description; aggregate the first and second pluralities of medical device information, log the aggregated first and second pluralities of medical device information to a system database; and display a visual rendering of the aggregated first and second pluralities of medical device information that is viewable on a graphical user interface; and an inventory module in operable communication with the processor, the inventory module operable to: prepare a list of a plurality of medical devices; and log the list of the plurality of medical devices in the system database.

2. The system of claim 1, wherein the first plurality of medical device information further comprises serial numberand date of manufacture.

3. The system of claim 1, wherein the processor is further adapted to generate an alert to the user if the medical device being scanned is within 90 days of the expiration date or past the expiration date.

4. The system of claim 3, wherein the alert is a visual indicator displayed on the interface.

5. The system of claim 1, wherein the second plurality of medical device information further comprises a manufacturer, package quantity, package type, and/or recall information.

6. The system of claim 5, wherein the processor is further adapted to generate an alert to the user if the medical device being scanned has an FDA recall.

7. The system of claim 6, wherein the alert is a visual indicator displayed on the interface.

8. The system of claim 1, wherein the inventory module is further operable to inventory the aggregated first and second pluralities of medical device information from the plurality of medical devices.

9. The system of claim 1, further comprising a document generator in operable communication with the computing device to transpose the aggregated first and second pluralities of medical device information for the plurality of medical devices from the system database to generate a document in a shareable format operable to be viewable on the graphical user interface and exported to an external user.

10. The system of claim 1, wherein the graphical user interface comprises a device details interface configured to receive manually inputted medical device information.

11. A method for facilitating the management of medical device inventory, the method comprising the steps of:

scanning, via a scanner integrated within a computing device, a barcode provided on a medical device for a first plurality of medical device information associated with the medical device, the first plurality of medical device information comprising at least an expiration date, lot number, and a unique device identifier (UDI);

interpreting, via a processor in communication with an interpreter, the first plurality of medical device information;

automatically pulling from a local database, via the processor, a second plurality of medical device information based on the interpreted first plurality of medical device information, wherein the second plurality of medical device information is stored on the local database comprising information from a Food and Drug Administration UDI database, the second plurality of medical device information comprising a model number and a device description;

aggregating the first and second pluralities of medical device information;

logging the aggregated first and second pluralities of medical device information into a system database;

preparing, via an inventory module in operable communication with the processor, a list of a plurality of medical devices; and logging the list of the plurality of medical devices and the inventory in the system database.

12. The method of claim 11, further comprising taking inventory of the aggregated first and second pluralities of medical device information from the plurality of medical devices.

13. The method of claim 11, further comprising:

displaying the aggregated first and second pluralities of medical device information via a graphical user interface on the computing device; and transposing, via a document generator, the aggregated first and second pluralities of medical device information from the system database into a document in a shareable format viewable on the graphical user interface.

14. The method of claim 13, further comprising exporting the document to an external user.

15. The method of claim 11, wherein the inventory module is operable to sort the aggregated medical device information and present the medical devices in an order.

16. The method of claim 11, further comprising the step of deleting all aggregated medical device information stored in the system database.

17. The method of claim 11, wherein the first plurality of medical device information further comprises a serial number and date of manufacture.

18. The method of claim 11, wherein the processor is further adapted to generate an alert to the user if the medical device being scanned is within 90 days of the expiration date or past the expiration date.

19. The method of claim 11, wherein the second plurality of medical device information further comprises a manufacturer, package quantity, package type, and/or recall information.

20. The method of claim 19, wherein the processor is further adapted to generate an alert to the user if the medical device being scanned has an FDA recall.

21. A computer-implemented system for medical device inventory management, the system comprising:

at least one scanner configured to scan a barcode provided on a medical device for a first plurality of medical device information associated with the medical device, the at least one scanner integrated within a computing device configured to receive the first plurality of medical device information from the scanner, wherein the first plurality of medical device information comprises at least a serial number, date of manufacture, and a unique device identifier (UDI) for the medical device;

a processor in operable communication with the computing device, the processor adapted to: interpret the first plurality of medical device information, via an interpreter; automatically pull from a local database a second plurality of medical device information associated with the medical device based on the interpreted first plurality of medical device information, wherein the second plurality of medical device information is stored on the local database comprising information from a Food and Drug Administration UDI database, the second plurality of medical device information comprising a model number and a device description; aggregate the first and second pluralities of medical device information, log the aggregated first and second pluralities of medical device information to a system database; and display a visual rendering of the aggregated first and second pluralities of medical device information that is viewable on a graphical user interface; and an inventory module in operable communication with the processor, the inventory module operable to: prepare a list of a plurality of medical devices; and log the list of the plurality of medical devices in the system database.

22. A method for facilitating the management of medical device inventory, the method comprising the steps of:

scanning, via a scanner integrated within a computing device, a barcode provided on a medical device for a first plurality of medical device information associated with the medical device, the first plurality of medical device information comprising at least a serial number, date of manufacture, and a unique device identifier (UDI);

interpreting, via a processor in communication with an interpreter, the first plurality of medical device information;

automatically pulling from a local database, via the processor, a second plurality of medical device information based on the interpreted first plurality of medical device information, wherein the second plurality of medical device information is stored on the local database comprising information from a Food and Drug Administration UDI database, the second plurality of medical device information comprising a model number and a device description;

aggregating the first and second pluralities of medical device information;

logging the aggregated first and second pluralities of medical device information into a system database;

preparing, via an inventory module in operable communication with the processor, a list of a plurality of medical devices; and logging the list of the plurality of medical devices and the inventory in the system database.

* * * * *